(12) United States Patent
Robson

(10) Patent No.: US 9,192,523 B2
(45) Date of Patent: Nov. 24, 2015

(54) SURGICAL ABSORPTIVE DEVICE AND METHODS OF USING THE SAME

(71) Applicant: Christine Robson, Portland, OR (US)

(72) Inventor: Christine Robson, Portland, OR (US)

(*) Notice: Subject to any disclaimer, the term of this patent is extended or adjusted under 35 U.S.C. 154(b) by 82 days.

(21) Appl. No.: 13/801,618

(22) Filed: Mar. 13, 2013

(65) Prior Publication Data

US 2013/0253462 A1 Sep. 26, 2013

Related U.S. Application Data

(60) Provisional application No. 61/615,028, filed on Mar. 23, 2012.

(51) Int. Cl.
| A61F 13/00 | (2006.01) |
| A61F 13/45 | (2006.01) |
| A61B 19/04 | (2006.01) |
| A61F 13/10 | (2006.01) |
| A41D 19/00 | (2006.01) |
| A61F 13/15 | (2006.01) |

(52) U.S. Cl.
CPC ............... *A61F 13/45* (2013.01); *A61B 19/04* (2013.01); *A61F 13/104* (2013.01); *A41D 19/0003* (2013.01); *A61F 2013/15048* (2013.01)

(58) Field of Classification Search
CPC ...... A61F 13/104; A61B 19/04; A41D 19/00; A41D 19/0003
USPC ........ 604/292, 362; 2/158, 159, 161.7, 161.8, 2/162, 163, 167
See application file for complete search history.

(56) References Cited

U.S. PATENT DOCUMENTS

| 2,210,754 A | | 8/1940 | Frank |
| 3,063,057 A | * | 11/1962 | Forman .......................... 2/161.6 |
| 3,263,681 A | | 8/1966 | Nechtow et al. |
| 3,409,010 A | * | 11/1968 | Kron ............................ 604/289 |
| 4,411,026 A | * | 10/1983 | Secter .............................. 2/158 |
| 4,658,444 A | | 4/1987 | Figlia et al. |
| 5,509,164 A | * | 4/1996 | Weill ............................. 15/222 |
| 5,708,980 A | * | 1/1998 | LaManna et al. ................. 2/163 |
| 5,766,248 A | | 6/1998 | Donovan |

(Continued)

FOREIGN PATENT DOCUMENTS

| JP | 3072962 U | 11/2000 |
| JP | 2007-070737 A | 3/2007 |

OTHER PUBLICATIONS

International Search Report for PCT/US2013/030921, mailed Jun. 26, 2013 (5 pages).

(Continued)

*Primary Examiner* — Lynne Anderson
(74) *Attorney, Agent, or Firm* — Klarquist Sparkman, LLP

(57) ABSTRACT

Methods of wearing a surgical device during a surgical procedure include putting the surgical device on a hand by passing the hand through a wrist cuff formed of a stretchable material of the surgical device and positioning the hand inside a first absorptive material of the surgical device that has been folded and secured together along at least a portion of its sides to form a pocket so that the surgical device is worn on the hand. The first absorptive material of the surgical device can be brought into contact with an internal surface of a patient while the surgical device is worn on the hand. Biological fluids in the vicinity of the surgical device can be absorbed by the first absorptive material when the first absorptive material is in contact with the internal surface of the patient.

20 Claims, 8 Drawing Sheets

(56) References Cited

U.S. PATENT DOCUMENTS

| | | |
|---|---|---|
| 5,807,296 A | 9/1998 | Stubbs |
| 6,280,529 B1 | 8/2001 | Meyer |
| 6,366,206 B1 * | 4/2002 | Ishikawa et al. ......... 340/573.1 |
| 6,539,549 B1 | 4/2003 | Peters |
| 6,647,548 B1 | 11/2003 | Lu et al. |
| 7,251,839 B2 * | 8/2007 | Bell .............................. 2/161.6 |
| 7,681,250 B2 * | 3/2010 | Friedstrom ...................... 2/158 |
| 7,874,020 B1 | 1/2011 | Franklin |
| 2008/0172767 A1 | 7/2008 | Friedstrom |
| 2009/0307858 A1 | 12/2009 | Gionet |

OTHER PUBLICATIONS

Written Opinion for PCT/US2013/030921, mailed Jun. 26, 2013 (7 pages).

Ayres III & Luikart. "Cotton glove in place of gauze for traction in surgical planing." *Archives of Dermatology*, 71.6 (1955): 744.

* cited by examiner

SURGICAL ABSORPTIVE DEVICE AND METHODS OF USING THE SAME

CROSS-REFERENCE TO RELATED APPLICATION

This application claims the benefit of U.S. Provisional Application No. 61/615,028, which was filed on Mar. 23, 2012 and is incorporated herein by reference in its entirety.

FIELD

This disclosure relates to a surgical aid and, more particularly to a surgical device that can worn on the hand and methods of using the same.

BACKGROUND

Surgeons and other medical personnel often use gauze for various purposes during surgical procedures. For example, during a surgical procedure, gauze mesh can be used to absorb biological fluids (e.g., blood), staunch bleeding, improve one's grip on a surgical instrument, and/or to facilitate gripping and holding body tissue (e.g., organs, skin, etc.) of the patient.

Gauze mesh for surgical applications is conventionally available in loose pieces that can be picked up and held by a surgeon or other medical staff member during a surgical procedure. For example, during a surgery, a surgeon or other medical staff member can grip one or more pieces of gauze mesh and place that material into contact with the patient or instrument to achieve a desired effect (e.g., absorption, improved grip, etc.). The use of loose pieces of gauze mesh, however, can create some difficulties. For example, it can be difficult or awkward to hold onto a piece of gauze mesh while attempting to perform the action for which the gauze is being used, such as grasping and retaining body tissue to aid in retraction of a surgical opening.

The loose form of conventional gauze mesh and other similar materials can also make those materials susceptible to being misplaced and/or retained within a patient after the surgery is completed. For example, according to occurrence rates described in a February 2011 edition of The Joint Commission Journal for Quality and Patient Safety, a surgical sponge is left behind in a patient once every 8,000 operations. Although sponge retainment in a patient is a relatively uncommon event, when one considers that that millions of surgical procedures are performed each year in the United States alone, the actual number of such occurrences is not insignificant. Moreover, the impact of sponge retainment (or the retainment of other similar objects), can be very hazardous to the health of the patient and, in some instances, can result in the patient's death.

Accordingly, it is desirable to provide improved surgical devices that can replace and/or supplement conventional gauze mesh materials to provide improved functioning and greatly improved risk management by reducing the occurrences of gauze misplacement and/or retainment within patients.

SUMMARY

Various surgical devices and methods of using such devices are described herein. In one embodiment, a wearable surgical device comprises a first absorptive material that has a first end, a second end, an outer surface, an inner surface, a first side, and a second side. The first absorptive material is folded over to form a folded portion so that a first area of the inner surface faces a second area of the inner surface. A first connecting portion attached to the first absorptive material secures a first portion of the first side with a second portion of the first side. A second connecting portion attached to the first absorptive material secures a third portion of the second side with a fourth portion of the second side. The folding of the absorptive material defines a pocket between the first area and the second area of the inner surface for receiving at least a portion of a hand of a user.

In some embodiments, only one connecting portion is provided on the lateral side of the device (i.e., the side that when the device is worn is the lateral side of the hand) and the other side of the device is secured by coupling the first absorptive material to itself.

In some embodiments, the first and second connecting portions are formed of a material that has a greater amount of flexibility than the first absorptive material. In some embodiments, the first and second connecting portions can be formed of a material that is thinner and less absorptive than the first absorptive material. In some embodiments, a third connecting portion is attached to the first absorptive material to secure the first end of the first absorptive material to the second end of the first absorptive material. The third connecting portion can comprise a wrist cuff.

In some embodiments, an opening can be provided between the wrist cuff and at least one of the first connecting portion and the second connecting portion. The opening can be sized to allow a thumb to pass through the opening when the surgical device is worn on the hand of a user. In other embodiments, the wearable surgical device can include a thumb cover extending between the wrist cuff and the first connecting portion or the second connecting portion, with the thumb cover forming an elongate pocket for receiving a thumb when the surgical device is worn on the hand of a user.

The materials of the first absorptive material and the connecting portions can vary. For example, in some embodiments, the material of the first absorptive material can comprise a cotton material or other material such as that used in connection with laparotomy sponges. Thus, for example, the absorbent material can comprise sterile, pre-washed cotton. In some embodiments, the absorbent material comprises surgical grade cotton gauze mesh. The absorbent material can be formed in various manners, shapes, and configurations. In some embodiments, for example, the absorbent material can be formed in a quilted-type pattern. The material of the connecting portions can comprise, for example, a stretchable material such as is used in Coflex tape or other elastic wraps. In some embodiments, the first, second, and third connecting portions are formed of the same material In some embodiments, the first area of the inner surface of the first absorptive material substantially overlaps with the second area of the inner surface of the first absorptive material. In some embodiments, an index finger cover can be provided that extends from either the first or second side of the surgical device. The index finger cover can comprise an elongate pocket for receiving an index finger when the surgical device is worn on the hand of a user.

In some embodiments, the wearable surgical device can include a radiopaque marker embedded therein. In other embodiments, the surgical device can be a single-use, disposable device.

In other embodiments, methods of wearing a surgical device during a surgical procedure are provided. The methods can include putting the surgical device on a hand by passing the hand through a wrist cuff formed of a stretchable material of the surgical device and positioning the hand inside a first absorptive material of the surgical device that has been folded and secured together along at least a portion of its sides to form a pocket so that the surgical device is worn on the hand. The first absorptive material of the surgical device can be brought into contact with an internal surface of a patient while the surgical device is worn on the hand. Biological fluids in the vicinity of the surgical device can be absorbed by the first absorptive material when the first absorptive material is in contact with the internal surface of the patient. In some embodiments, the act of wearing the surgical device can include placing a surgical glove on the hand before passing the hand through the wrist cuff. In this manner, the surgical device can be worn over the surgical glove.

In some embodiments, the method can further include gripping a surgical instrument in the hand while wearing the surgical device on the hand, wherein contact of the first absorptive material of the surgical device provides increased frictional contact with the surgical instrument. In other embodiments, the method can further include gripping an organ or other internal tissue of the patient in the hand while wearing the surgical device on the hand, wherein contact of the first absorptive material of the surgical device provides increased frictional contact with the organ or other internal tissue.

In some embodiments, the act of wearing the surgical device comprises extending a thumb on the hand through an opening in the surgical device so that the thumb is not enveloped by the surgical device when the surgical device is worn on the hand. In other embodiments, the act of wearing the surgical device comprises extending a thumb on the hand into an elongate pocket of the surgical device so that the thumb is enveloped by the surgical device when the surgical device is worn on the hand.

In some embodiments, a wearable surgical device comprises a first side formed of a first absorptive material, a second side formed of a second absorptive material, a wrist cuff for securing the surgical device to the wrist of a user, and first and second openings sized to allow a thumb to pass through the openings when the surgical device is worn on the hand of a user. The first and second openings are on opposing sides of the surgical device so that the surgical device can be rotated by the wearer to present either the first side or the second side on the palm side of the user's hand.

In some embodiments, the surgical device is a one-time use device and the method includes disposal of the surgical device after the surgical procedure so that it is not reused during another surgical procedure.

The foregoing and other objects, features, and advantages of the invention will become more apparent from the following detailed description, which proceeds with reference to the accompanying figures.

DETAILED DESCRIPTION

Various embodiments of devices for use in surgical and other similar types of environments and their methods of use are described herein. The following description is exemplary in nature and is not intended to limit the scope, applicability, or configuration of the invention in any way. Various changes to the described embodiments may be made in the function and arrangement of the elements described herein without departing from the scope of the invention. As used in this application and in the claims, the terms "a," "an," and "the" include both the singular and plural forms of the element(s) they refer to unless the context clearly dictates otherwise. Additionally, the term "includes" means "comprises."

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The devices described herein can be used in a variety of procedures, including any surgical procedure on a patient. Such surgical procedures can include, for example, bariatric, breast, urogynecological, obstetric, cardiac, abdominal and gastroenterological, and orthopedic procedures. In addition as used herein, the term "patient" refers to any human or non-human undergoing a surgical procedure. Thus, for example, the devices and methods described herein can be utilized in a veterinary surgical procedure.

In some embodiments, the devices described herein can advantageously be used in other non-surgical environments where the attributes noted above (e.g., absorptiveness, gripping ability, etc.) may be desirable. For example, in some embodiments, the devices described herein can be used to connection with organ and tissue harvesting from patients and/or cleaning or dressing an animal after fishing or hunting.

Figure 1:
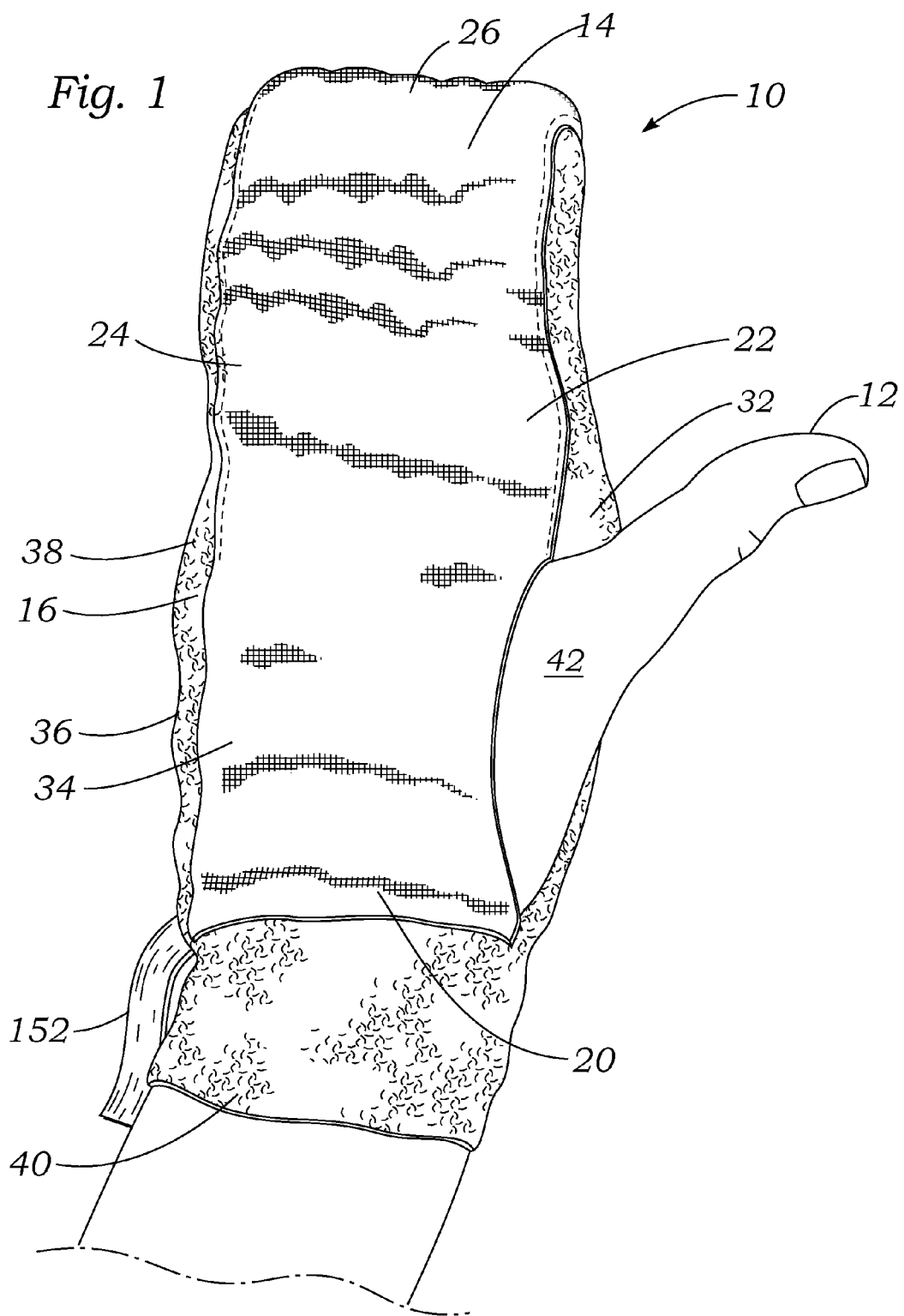
FIG. 1 illustrates a top view of a medical device that can be worn on the hand of a user during a procedure.
Figure 2:
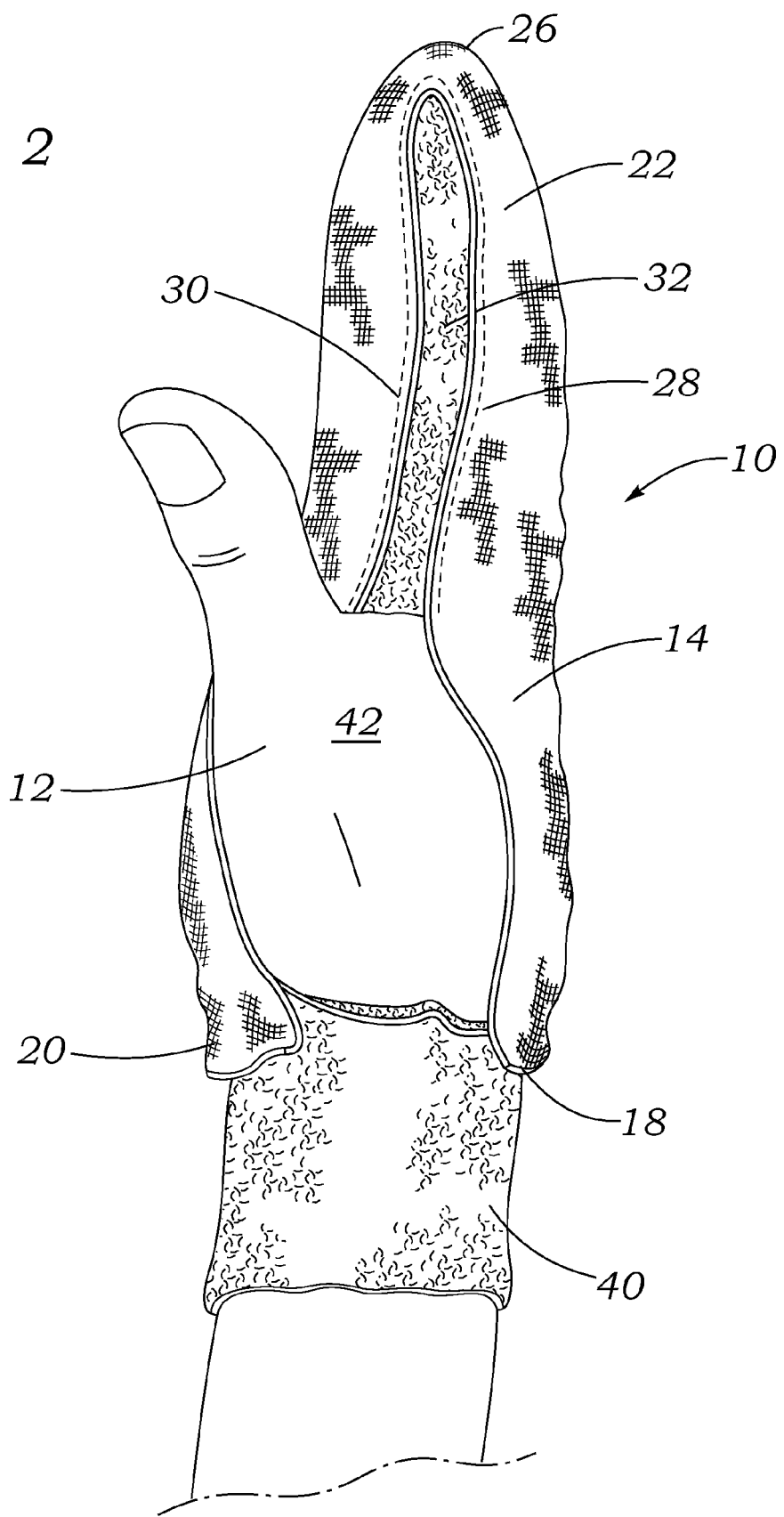
FIG. 2 illustrates a side view of a medical device that can be worn on the hand of a user during a procedure.

FIGS. 1 and 2 illustrate a surgical device 10 that is configured to be worn on a hand 12. Surgical device 10 comprises a first absorptive material 14 and a second material 16. First absorptive material can comprise a generally elongate material with a first end 18, a second end 20, and two sides 22, 24. The first absorptive material 14 can be folded over on itself to form a folded portion 26. When first absorptive material 14 is folded over on itself, an inner surface and an outer surface is established, with the inner surface forming a pocket for receiving at least a portion of a hand.

As shown in FIG. 2, when first absorptive material 14 is folded, a first portion 28 of the first side 22 is brought into the vicinity of a second portion 30 of the first side 22. A first connecting portion 32 is formed from second material 16 and attached to the first absorptive material 14 to secure the first and second portions 28, 30 to one another. Similarly, with respect to the second side 24, a third portion 34 and a fourth portion 36 of the second side 24 are brought into the vicinity of one another and second connecting portion 38 is formed from second material 16 and attached to the first absorptive material 14 to secure the third and fourth portions 34, 36 to one another.

The first absorptive material 14 can comprise an absorptive material that is capable of absorbing fluids upon contact, such as surgical grade gauze. In some embodiments, the first absorptive material 14 can be formed of the same materials or similar materials to those conventionally used in, for example, laparotomy sponges. The second material 16 can comprise any suitable connecting material and is preferably more flexible than the first absorptive material 14 so that it can stretch to conform to the hand 12 as necessary. In addition, the ability to flex upon receiving the hand within the surgical device 10 permits the second material 16 to more securely retain the hand within the surgical device.

Additional material can be provided in the wrist area of a wearer. For example, third connecting portion 40 can be secured to the first absorptive material 14 and/or to the other connecting portions 32, 38 to provide addition structure to surgical device 10. As shown in FIGS. 1 and 2, third connecting portion 40 can comprise a wrist cuff that extends around the wrist of the wearer. In the embodiment shown in FIGS. 1 and 2, the wrist cuff is attached along one side to the first end 18 and the second end 20, as well as to a portion of at least one of the connecting portions (e.g., connecting portion 38).

As shown in FIGS. 1 and 2, an opening 42 in surgical device 10 can be provided between the wrist cuff 40 and at least one of the connecting portions (e.g., connecting portion 32). Opening 42 can be sized so that a thumb of the hand 12 can pass through the opening and extend out of surgical device 10. In some embodiments, openings can be formed on both sides of surgical device 10, so that surgical device 10 can be worn on either hand. That is, in one orientation for receiving a right hand of a wearer, the right thumb of a wearer can extend through an opening on one side of surgical device 10 and, when the same surgical device is flipped over into the mirror-opposite orientation for receiving the left hand of a wearer, the left thumb of a wearer can extend through an opening on the other side of surgical device 10.

Figure 3:
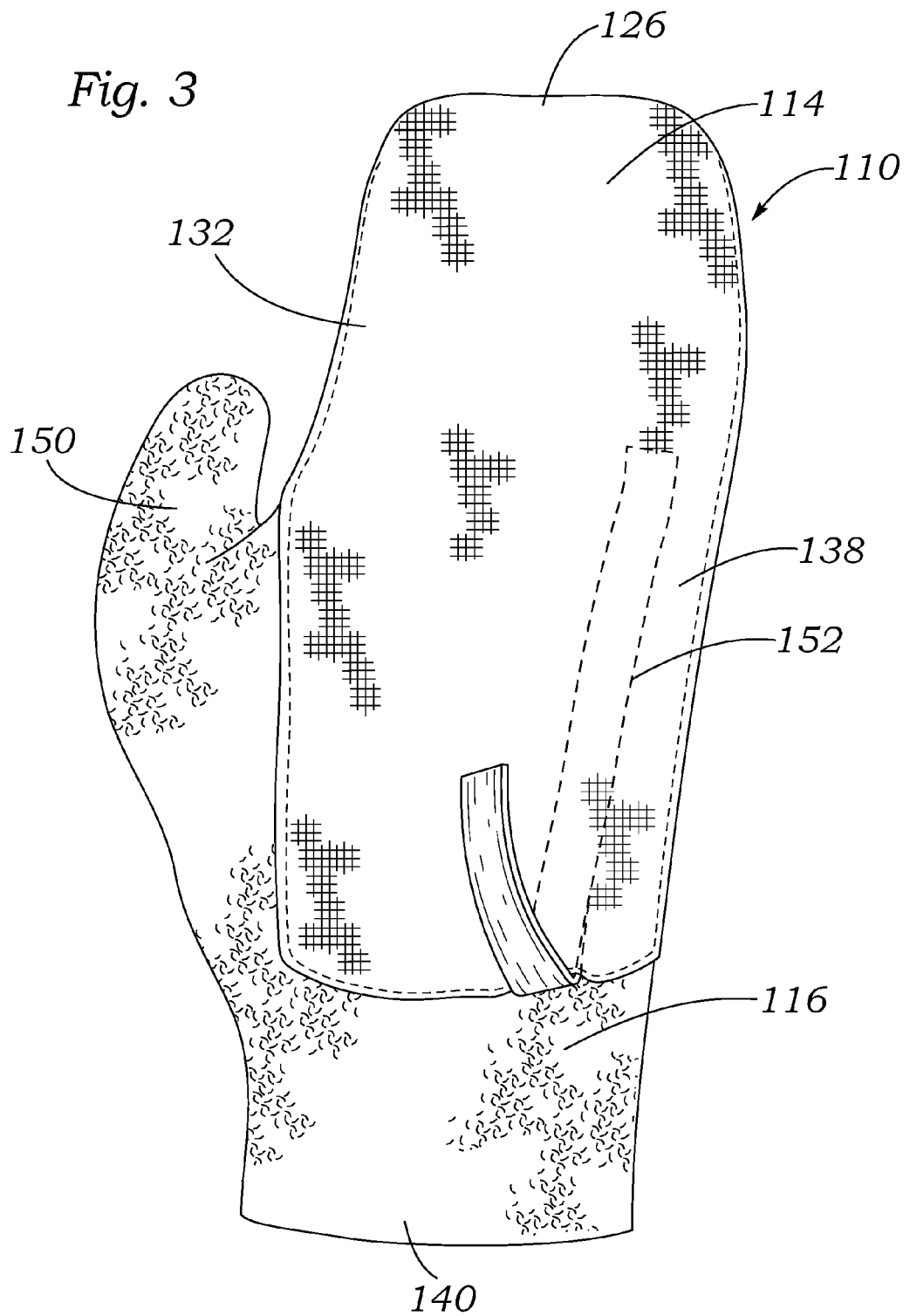
FIG. 3 illustrates a top view of a medical device that can be worn on the hand of a user during a procedure, with the device having a thumb covering area.

FIG. 3 illustrates another embodiment of a surgical device 110. Surgical device 110 is similar to surgical device 10 and, therefore, for convenience, like components are indicated by like references numerals. For example, first absorptive material is identified by reference numeral 14 in FIG. 1 and by reference numeral 114 in FIG. 3.

Surgical device 110 comprises a thumb cover 150 extending between the wrist cuff 140 and the first connecting portion 132. Thumb cover 150 forms an elongate pocket for receiving a thumb when surgical device 110 is worn on the hand.

The surgical devices disclosed herein can be used during surgical procedures to control hemostasis and improve risk management by greatly reducing the use of loose absorptive materials, such as laparotomy sponges, that must be gripped (instead of worn) for use. Loose absorptive materials, such as laparotomy sponges, can be subject to misplacement. Such misplacement results in significant expended effort in locating the loose materials and, in some extreme cases, can result in the loose material being retained within the body of the patient, an event which is highly undesirable because of the potential harm of such retention to the patient. In contrast, the surgical devices described herein are configured to be worn by a surgeon or medical personnel, thereby allowing for better control and location of the surgical device during and after completion of the surgical procedure.

Surgical procedures generally require that the surgeon and other medical staff members attending to the surgery wear surgical gloves on their hands. Accordingly, the surgical devices disclosed herein can be sized to be worn over a gloved hand of the surgeon or other medical personnel. Although the figures do not illustrate a surgical glove, one of ordinary skill in the art would understand that a surgical glove is generally relatively tight fitting and therefore the profile of a hand without a glove is substantially the same as the profile of a hand wearing a glove. Since wearing the surgical devices over surgical gloves reduces contact of the surgical gloves themselves with fluids during a surgery, the surgical devices disclosed herein can reduce the need for multiple glove changes during surgeries where large amounts of fluids are present.

As shown in FIGS. 1 and 2, first absorptive material 14 can extend along the length of the surgical device about an equal amount on both sides of the surgical device so that a first area (e.g., top-of-hand facing area) of the first absorptive material 14 substantially overlaps with a second area (e.g., palm facing area) of the first absorptive material 14. For example, as shown in FIG. 2, on the top surface of the hand 12 and the bottom surface of the hand 12, first absorptive material 14 extends to the wrist cuff 40.

Figure 4:
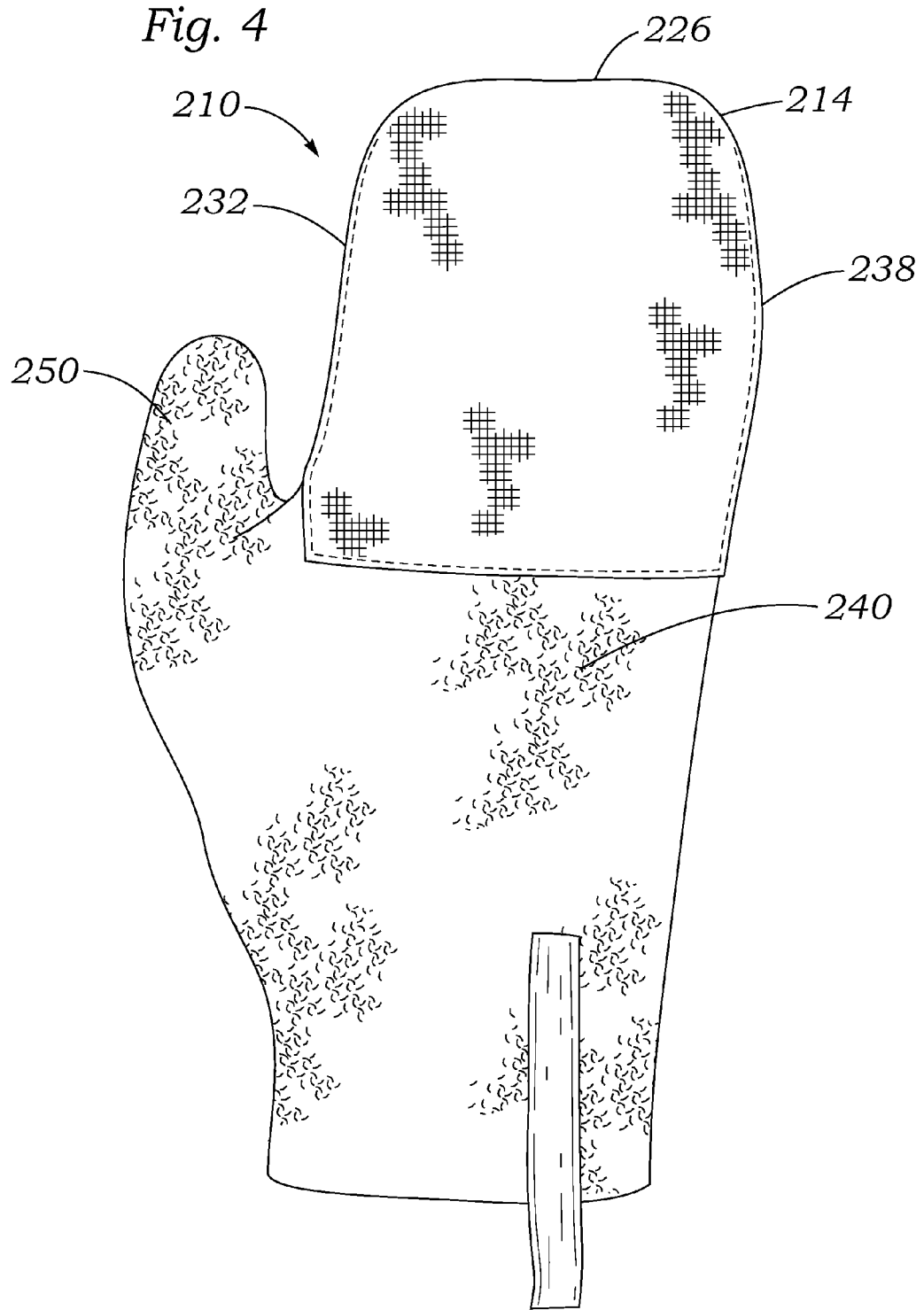
FIG. 4 illustrates a top view of a medical device that can be worn on the hand of a user during a procedure, with the device having a thumb covering area.

The symmetrical arrangement of the first absorptive material 14 in this manner permits reversibility of the surgical device so that it can be worn on either hand to the same effect. In other embodiments, however, it should be understood that the first absorptive material can extend different amounts on the two opposing sides of the surgical device. In addition, it should be understood that the first absorptive material need not extend entirely to the wrist area. Instead, for example, first absorptive material can extend to cover a finger area of the hand, but not the palm (or back of the hand) portion of the hand. For example, FIG. 4 illustrates a surgical device 210 that comprises a first absorptive material that does not extend to the wrist when worn on a hand. Instead, surgical device 210 extends only to entirely cover the fingers of the wearer.

In use, the surgical device can be placed on the hand by passing a hand through the wrist cuff and positioning the hand inside a first absorptive material so that at least some of the fingers of the hand are in the pocket created by the first absorptive material. By covering at least some of fingers with the first absorptive material, the wearer can move their hand (with the surgical device thereon) into the contact with an internal surface of a patient. Such contact permits biological fluids in the vicinity of the surgical device to be absorbed into the first absorptive material.

In addition, compared to a gloved hand, the first absorptive material can provide increased frictional contact with whatever the surgeon or medical personnel needs to touch or grab. For example, when wearing the surgical devices described herein, the fingers of the surgeon or medical personnel can more easily grip medical instruments or tissue of the patient when wearing the first absorptive material over their fingers, both because of the removal of fluids in the area and because of the surface of the first absorptive material itself.

After using the surgical devices in the surgical procedure, the surgical devices can be disposed of in a safe manner so that they are not accidentally reused for any other procedure. The surgical devices described herein can be packaged in a sterile manner so that medical personnel will know not to use devices that are not in their original packaging.

In constructing the surgical devices described herein, it should be understood that the connecting portions can be formed of separate material (e.g., Coflex™) that is stitched together or otherwise attached to the first absorptive material and/or each other. However, the manner of attachment can vary and the specific manner of attachment (e.g., the illustrated stitching along portions of the device as shown in the figures) is not intended to be limiting in nature. Alternatively, the connecting portions can be formed of one piece of material as shown in FIG. 4 (discussed in more detail below). In addition, if desired, connecting portions or other similar materials can extend under first absorptive material (either partially or entirely), forming an underlayer to the first absorptive material.

In some embodiments, the entire device can be constructed of one material, such as the first absorptive material. In that case, the portions identified as connecting portions would be constructed using the first absorptive material. In addition, instead of stitching various separate pieces together, in such embodiments, the device could be formed from one piece of material.

FIG. 4 illustrates connecting portions 232, 234, and 240 formed of a single piece of stretchable material to which the first absorptive material 214 is attached. In addition, thumb cover 250 is also formed of the same material as the connecting portions. If desired, the single piece of stretchable material can extend beneath the first absorptive material so that the first absorptive material substantially overlaps the stretchable material.

In some embodiments, a radiopaque marker can be provided on the surgical device to facilitate location of the surgical device within the patient if necessary. For example, as shown in FIGS. 1 and 3, radiopaque marker 152 can be attached to surgical device 10, 110 at any desirable location on the surgical device. Because the surgical devices described herein are worn rather than simply held, however, they are significantly less likely to be accidentally retained within the body of the patient and, therefore, the radiopaque marker is optional.

Alternatively, other tracking systems can be provided in combination with the devices described herein. For example, an RFID member can be provided on the devices to facilitate location of lost devices during surgical procedures.

Figure 5:
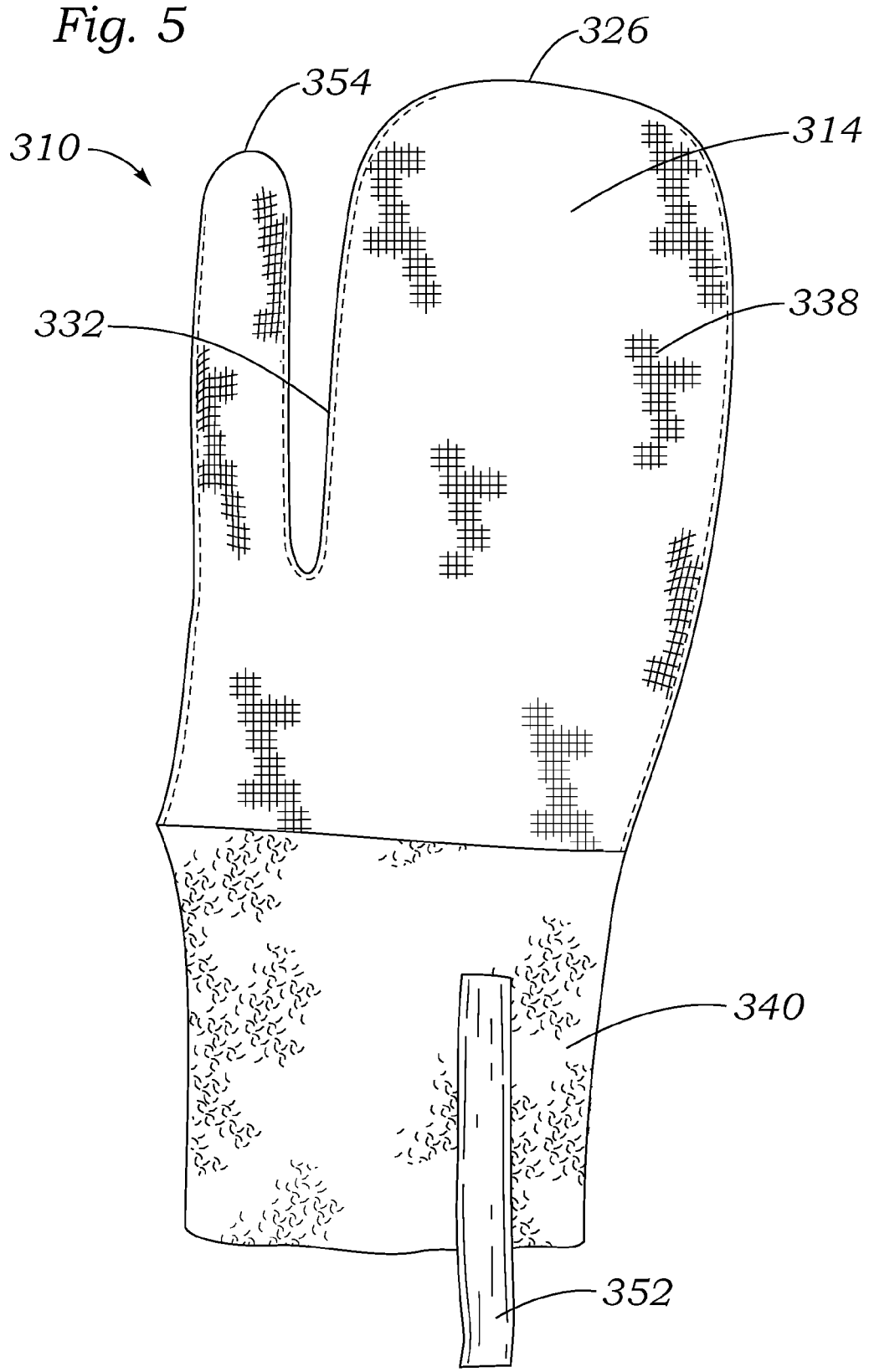
FIG. 5 illustrates a top view of a medical device that can be worn on the hand of a user during a procedure, with the device having an index finger covering area.
Figure 6:
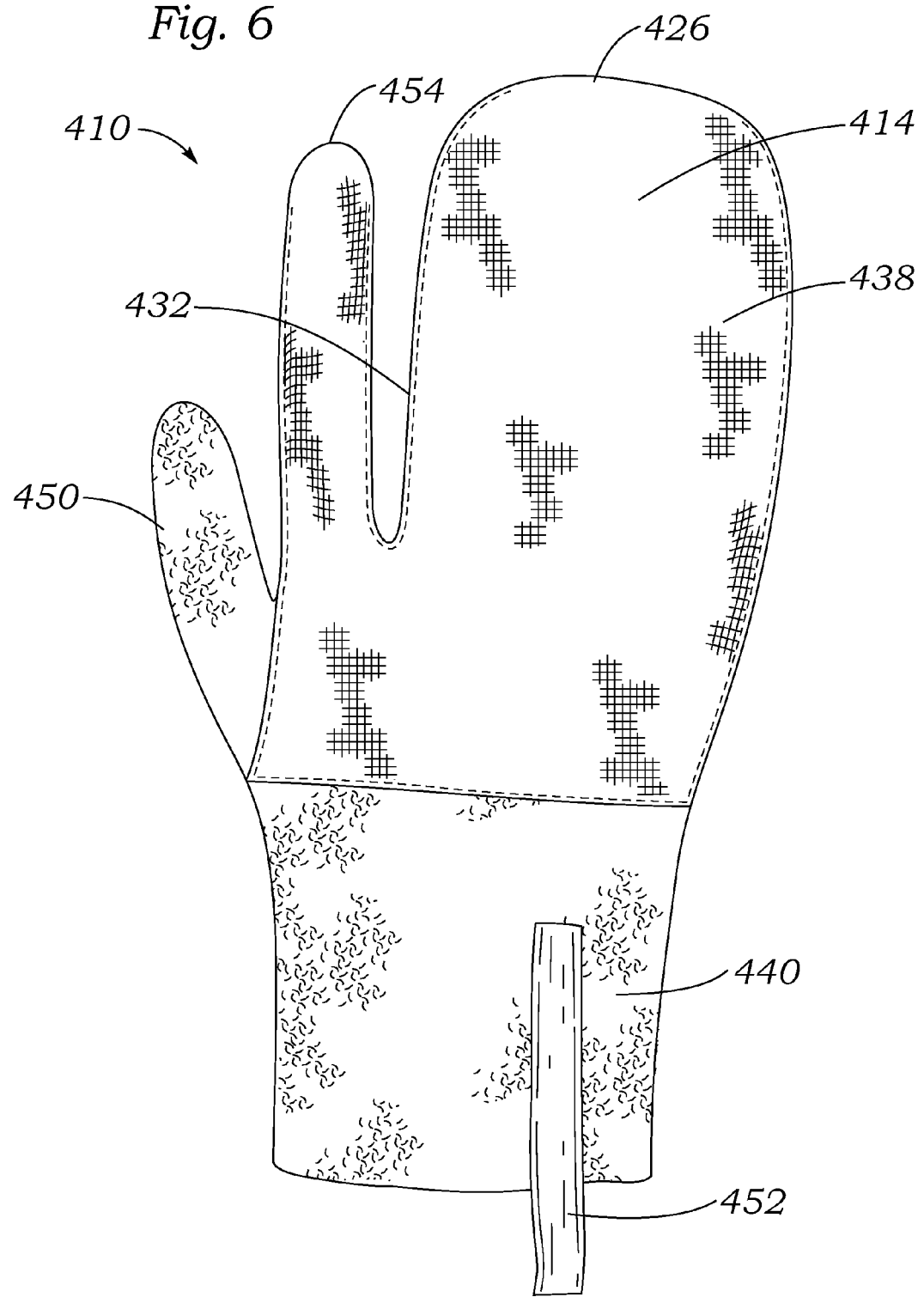
FIG. 6 illustrates a top view of a medical device that can be worn on the hand of a user during a procedure, with the device having an index finger covering area and a thumb covering area.

Although first absorptive material 14 is shown in the embodiments as a generally rectangular shape that is folded over to form a pocket for receiving a hand, it should be understood that other shapes can be used. For example, the sides and/or ends can be curved, if desired, to better conform to the shape of the hand. In addition, if desired, one or more separate finger covers can be provided formed of the first absorptive material. For example, FIGS. 5 and 6 illustrate additional embodiments wherein an index finger cover extends from the surgical device, the index finger cover comprising an elongate pocket for receiving an index finger when the surgical device is worn on the hand of a user. FIG. 5 illustrates surgical device 310 with an index finger cover 354 and no thumb cover, while FIG. 6 illustrates surgical device 410 with an index finger cover 454 and a thumb cover 450. By providing a separate index finger cover as shown in FIGS. 5 and 6, additional mobility can be provided to the surgical devices which can, in turn, provide increased gripping capabilities for the wearer.

Although the embodiments discussed above generally illustrate the use of connecting portions on both sides of the hand, it should be understood that only one connecting portion could be provided. Thus, for example, the device of FIG. 1 could be modified to eliminate connecting portion 38 so that only the connecting portion 32 on the lateral side of the hand remains. In this embodiment, the side 24 of the absorptive material can be coupled to the other side that is folded over. Of course, this arrangement may result in a reduced amount of flexibility of the device in conforming to different sizes of hands.

Figure 7:
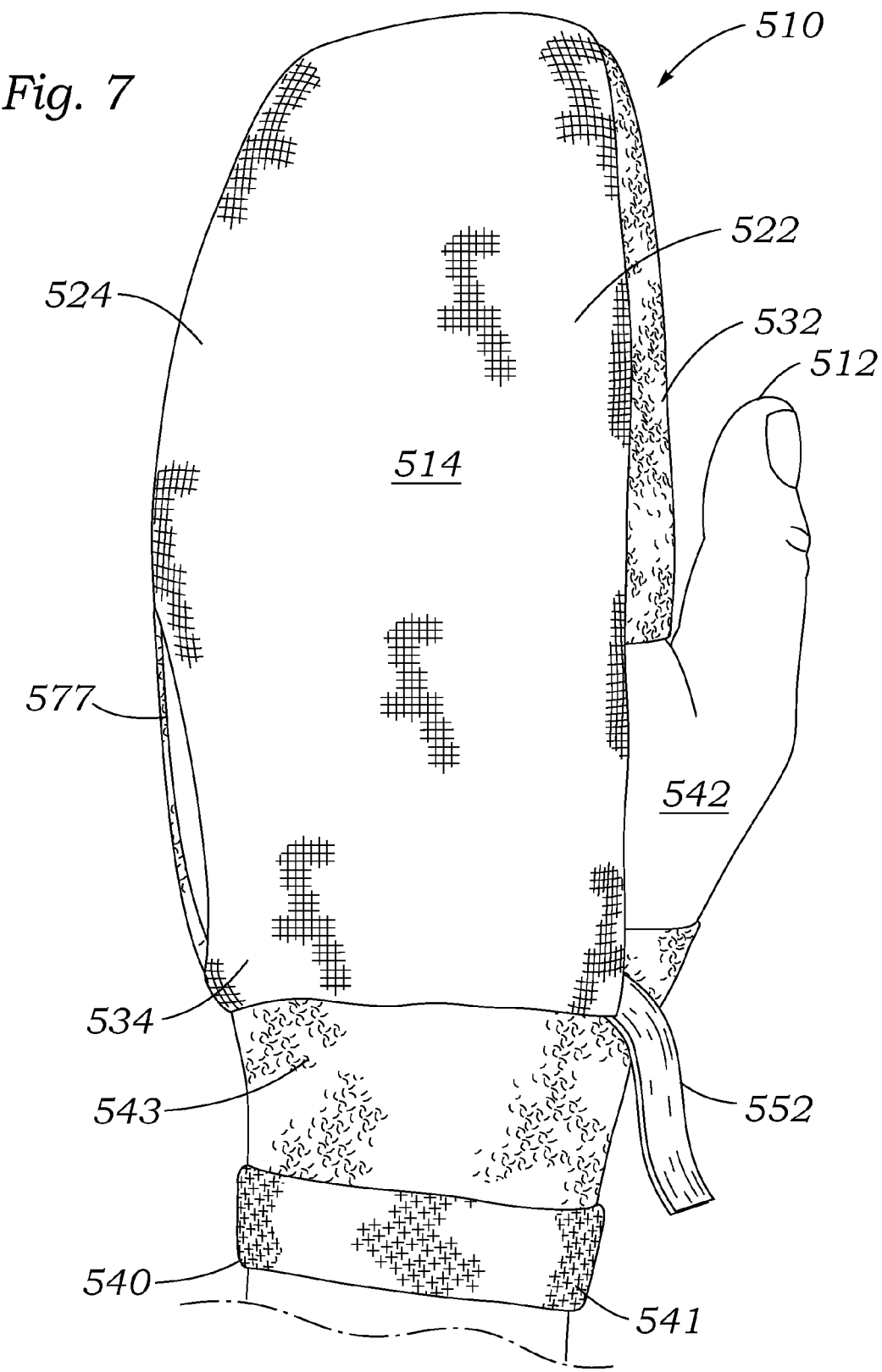
FIG. 7 illustrates a view of a medical device that can be worn on either hand of a user during a procedure.
Figure 8:
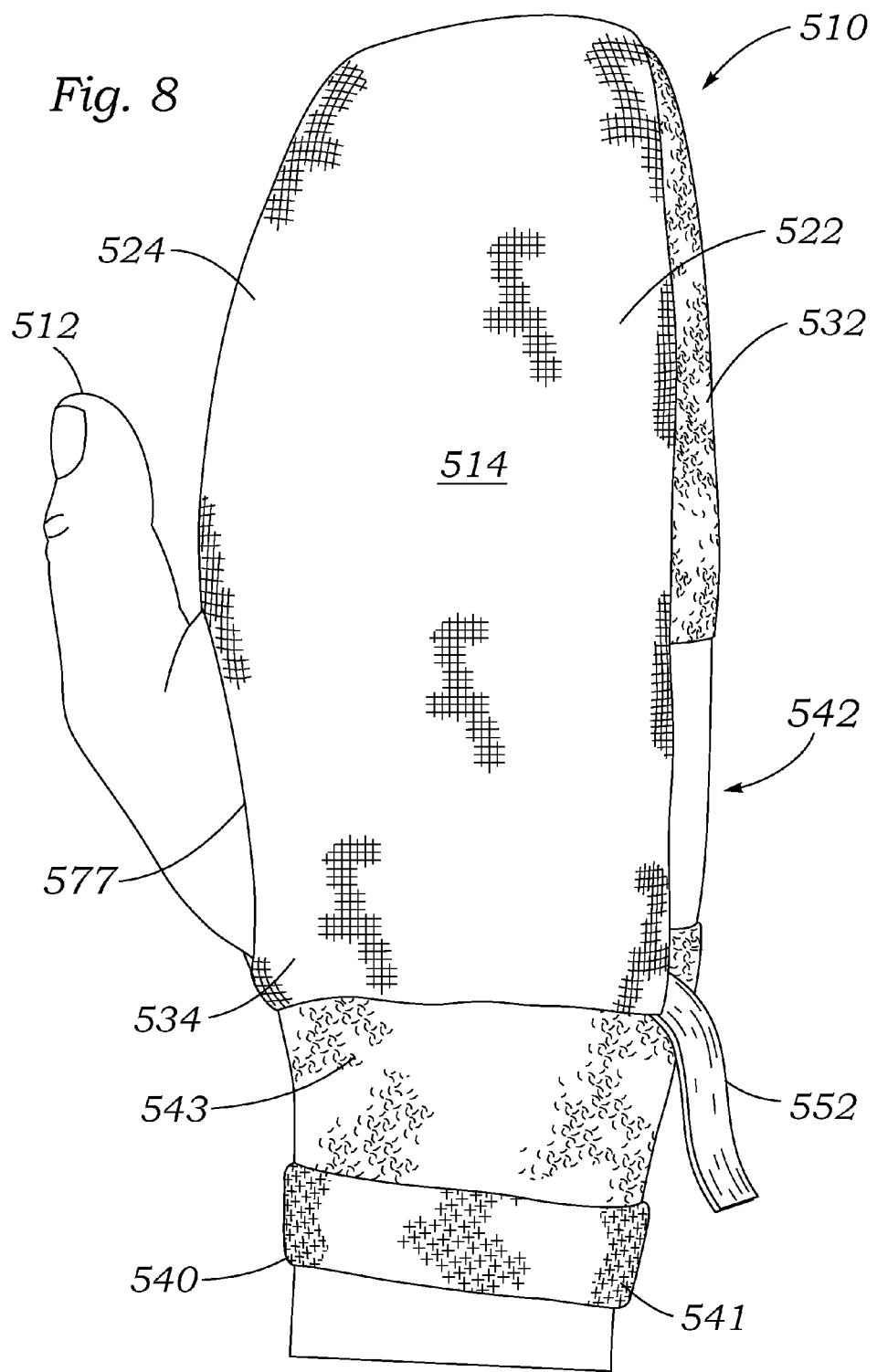
FIG. 8 illustrates another view of the medical device of FIG. 7.

As shown in FIGS. 7 and 8, openings can be provided on both sides of the surgical device to allow the device to be used on either hand and/or to allow the device to be reversed on the same hand to achieve greater absorption of fluids. For example, FIGS. 7 and 8 illustrate a device similar to that of FIG. 1, but including both a first opening 542 and a second opening 577. FIG. 7 illustrates the device worn on the left hand and FIG. 8 illustrates the device worn on the right hand.

As discussed above, openings in both sides can permit the device to be worn on either hand. Therefore, during a procedure it can be put on quickly, without concern that the device is not aligned properly for that hand. In addition, having openings on both sides advantageously allows a wear to quickly reverse the device on the same hand during a procedure. By reversing the device, a new surface (i.e., the opposing exterior surface of the device) can be presented for further absorption of fluids or for a new "dry" surface for gripping or performing any other desired action.

In this manner, during a surgical procedure a user can present a first surface of the device for gripping and/or absorbing fluid and the like. Then, the user can quickly rotate the device (e.g., 180 degrees) on the hand so that a second surface (i.e., the opposing exterior surface) is presented for gripping and/or absorbing fluid and the like.

As described herein, various materials and configurations can be formed of multiple materials. For example, in some implementations, the wrist cuff can comprise two or more different materials as shown in FIGS. 7 and 8. For example, wrist cuff 540 can include a closure material 541 with a narrower opening and/or greater elasticity than a second transition material 543 positioned between the closure material 541 and the absorptive material 514 (e.g., gauze, etc.).

As described above, the surgical devices disclosed herein provide significant advantages over conventional hand-held sponges or other loose materials that are currently used during surgical procedures. These benefits include, for example, greater control while grasping items (instruments or patient tissue) during a surgical procedure and a reduced likelihood that the surgical device will be lost during the procedure compared to loosely-held materials such as sponges. In addition, because of the flexible connecting portions, the surgical devices described herein can conform to fit hands of different sizes, providing a one-size-fits-all solution. In addition, in some embodiments, the surgical devices can be configured to be worn on either hand, increasing the flexibility of their use.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A wearable surgical device comprising:
   a first absorptive material that has a first end, a second end, an outer surface, an inner surface, a first side, and a second side, the first absorptive material being folded over to form a folded portion so that a first area of the inner surface faces a second area of the inner surface;
   a first connecting portion attached to the first absorptive material to secure a first portion of the first side with a second portion of the first side;

a second connecting portion attached to the first absorptive material to secure a third portion of the second side with a fourth portion of the second side; and a pocket between the first area and the second area of the inner surface for receiving at least a portion of a hand of a user, wherein the first and second connecting portions are formed of a material that has a greater amount of flexibility than the first absorptive material.

2. The wearable surgical device of claim 1, wherein the first and second connecting portions are formed of a material that is thinner and less absorptive than the first absorptive material.

3. The wearable surgical device of claim 1, further comprising a third connecting portion attached to the first absorptive material to secure the first end of the first absorptive material to the second end of the first absorptive material.

4. The wearable surgical device of claim 3, wherein the third connecting portion comprises a wrist cuff.

5. The wearable surgical device of claim 4, further comprising a first opening between the wrist cuff and at least one of the first connecting portion and the second connecting portion, the first opening being sized to allow a thumb to pass through the opening when the surgical device is worn on the hand of a user.

6. The wearable surgical device of claim 5, further comprising a second opening between the wrist cuff and at least one of the first connecting portion and the second connecting portion, the second opening being sized to allow a thumb to pass through the opening when the surgical device is worn on the hand of a user.

7. The wearable surgical device of claim 4, further comprising a thumb cover extending between the wrist cuff and the first connecting portion or the second connecting portion, the thumb cover forming an elongate pocket for receiving a thumb when the surgical device is worn on the hand of a user.

8. The wearable surgical device of claim 3, wherein the first, second, and third connecting portions are formed of the same material.

9. The wearable surgical device of claim 1, wherein the first area of the inner surface of the first absorptive material substantially overlaps with the second area of the inner surface of the first absorptive material.

10. The wearable surgical device of claim 1, further comprising an index finger cover extending from either the first or second side of the surgical device, the index finger cover comprising an elongate pocket for receiving an index finger when the surgical device is worn on the hand of a user.

11. The wearable surgical device of claim 1, wherein the absorbent material comprises surgical grade cotton gauze mesh.

12. The wearable surgical device of claim 1, further comprising a radiopaque marker.

13. The wearable surgical device of claim 1, wherein the surgical device is disposable after one use.

14. A wearable surgical device comprising:
a first absorptive material that has a first end, a second end, an outer surface, an inner surface, a first side, and a second side, the first absorptive material being folded over to form a folded portion so that a first area of the inner surface faces a second area of the inner surface;

a first connecting portion attached to the first absorptive material to secure a first portion of the first side with a second portion of the first side;

a second connecting portion attached to the first absorptive material to secure a third portion of the second side with a fourth portion of the second side; and a pocket between the first area and the second area of the inner surface for receiving at least a portion of a hand of a user, wherein the first and second connecting portions are formed of a material that is thinner and less absorptive than the first absorptive material.

15. The wearable surgical device of claim 14, further comprising a third connecting portion attached to the first absorptive material to secure the first end of the first absorptive material to the second end of the first absorptive material, wherein the third connecting portion comprises a wrist cuff.

16. The wearable surgical device of claim 15, further comprising a first opening between the wrist cuff and at least one of the first connecting portion and the second connecting portion, the first opening being sized to allow a thumb to pass through the opening when the surgical device is worn on the hand of a user.

17. The wearable surgical device of claim 14, further comprising an index finger cover extending from either the first or second side of the surgical device, the index finger cover comprising an elongate pocket for receiving an index finger when the surgical device is worn on the hand of a user.

18. The wearable surgical device of claim 14, wherein the absorbent material comprises surgical grade cotton gauze mesh.

19. A wearable surgical device comprising:
a first absorptive material that has a first end, a second end, an outer surface, an inner surface, a first side, and a second side, the first absorptive material being folded over to form a folded portion so that a first area of the inner surface faces a second area of the inner surface;

a first connecting portion attached to the first absorptive material to secure a first portion of the first side with a second portion of the first side;

a second connecting portion attached to the first absorptive material to secure a third portion of the second side with a fourth portion of the second side;

a pocket between the first area and the second area of the inner surface for receiving at least a portion of a hand of a user, and a third connecting portion attached to the first absorptive material to secure the first end of the first absorptive material to the second end of the first absorptive material, wherein the first, second, and third connecting portions are formed of the same material.

20. The wearable surgical device of claim 19, wherein the absorbent material comprises surgical grade cotton gauze mesh.

* * * * *